United States Patent [19]
Tembe et al.

[11] Patent Number: 6,121,502
[45] Date of Patent: *Sep. 19, 2000

[54] PROCESS FOR MANUFACTURE OF LINEAR ALPHA-OLEFINS USING A TITANIUM COMPONENT AND AN ORGANOALUMINUM HALIDE COMPONENT

[75] Inventors: Gopal Laxman Tembe; Ashis Ranjan Bandyopadhyay; S. Muthukumaru Pillai; Sheo Satish; M. Ravindranathan, all of Gujarat, India

[73] Assignee: Indian Petrochemicals Corporation Limited, Gujarat, India

[ * ] Notice: This patent issued on a continued prosecution application filed under 37 CFR 1.53(d), and is subject to the twenty year patent term provisions of 35 U.S.C. 154(a)(2).

[21] Appl. No.: 08/802,062

[22] Filed: Feb. 19, 1997

[51] Int. Cl.$^7$ .................................. C07C 2/02; C07C 2/24
[52] U.S. Cl. .......................... 585/524; 585/511; 585/512; 585/513; 585/514; 585/515; 585/521; 585/526; 585/528; 585/532

[58] Field of Search ........................... 585/502, 510–515, 585/520, 521, 524, 526, 528, 532

[56] References Cited

U.S. PATENT DOCUMENTS

| | | | |
|---|---|---|---|
| 4,689,437 | 8/1987 | Murray | 585/526 |
| 4,737,479 | 4/1988 | Frame et al. | 502/117 |
| 4,870,041 | 9/1989 | White | 585/524 |
| 5,146,028 | 9/1992 | Job | 585/512 |

FOREIGN PATENT DOCUMENTS 787438  12/1957  United Kingdom .

*Primary Examiner*—Walter D. Griffin
*Assistant Examiner*—In Suk Bullock
*Attorney, Agent, or Firm*—Ladas & Parry

[57] ABSTRACT

A process for the manufacture of linear alpha-olefins is disclosed. The process employs, for the purposes of oligomerizing an unsaturated aliphatic hydrocarbon to linear alpha-olefins, a catalyst mixture comprising titanium aryl and/or titanium alkoxide, organoaluminum halide and optionally one or more additives selected from a group containing phosphorus, oxygen and sulphur compounds.

24 Claims, No Drawings

PROCESS FOR MANUFACTURE OF LINEAR ALPHA-OLEFINS USING A TITANIUM COMPONENT AND AN ORGANOALUMINUM HALIDE COMPONENT

FIELD OF THE INVENTION

The present invention relates to a process for the manufacture of linear alpha-olefins. More particularly, the invention comprises the manufacture of linear alpha-olefins by oligomerizing unsaturated aliphatic hydrocarbons. More particularly, the invention relates to the manufacture of alpha-olefins by oligomerizing unsaturated aliphatic hydrocarbons in the presence of a catalyst system which is a mixture of
1) titanium aryloxide and/or titanium alkoxide; and
2) organoaluminum halide; and
3) optionally at least one phosphorous, oxygen or sulphur compound.

Still more particularly, the invention relates to the manufacture of alpha-olefins by oligomerizing ethylene in the presence of a catalyst system which is a mixture of 1) titanium aryloxide and/or titanium alkoxide and 2) organoaluminum halide and 3) optionally at least one phosphorous, oxygen or sulphur compound.

The process of the invention is useful in producing predominantly highly linear, low molecular weight alpha-olefins from ethylene.

BACKGROUND OF THE INVENTION

Alpha-olefins in the range of 4–40 carbon atoms are known to be prepared by wax cracking, paraffin dehydrogenation and dehydration of alcohols. However, these processes suffer from the drawback of low conversion, low product purity of specific alpha-olefins and high energy costs.

Other widely used processes to prepare alpha-olefins are based on ethylene chain growth and displacement reactions [Ziegler]. These processes utilize trialkyl aluminum, particularly triethylaluminum at high temperatures [170–200° C.] and pressures [140 atm]. A particular drawback of such processes is the difficulty in the separation of lighter and higher olefins and the formation of internal and vinylidene olefins.

Several patents known hereto before disclose the catalytic low temperature oligomerization of ethylene based on titanium halide [e.g. $TiCl_4$], alkyl aluminum halide [e.g. $EtAlCl_2$] [Ziegler-Natta] modified by phosphines [e.g. $nBu_3P$]. The selectivity of alpha-olefins in these cases is affected by copolymerization reactions yielding undesirable branched olefins.

British Patent No. 787,438, issued on Dec. 11, 1957 describes the preparation of lower alpha-olefins with less than 6 carbon atoms which are prepared by utilizing a catalyst prepared by combining titanium tetraalkoxide and triethylaluminum. This process involves moderate ethylene conversions.

Low temperature oligomerization by halogenated titanium alkoxides yielding alpha olefins up to $C_{50}$ is disclosed in German Patent No. 1,924,427, issued on Apr. 23, 1970. Another class of catalysts which have been utilized are organoaluminum-free compounds [non-Ziegler] [e.g. $Ni(COD)_2$ or nickel ylides] which are used to convert ethylene to higher oligomers of even carbon numbers [e.g. $C_4$–$C_{20+}$] which are linear in character. The non-Ziegler route using bis [cyclooctadiene] nickel [o] or its complexes with fluorinated compounds [e.g. hexafluoroacetyl acetone] is described in the U.S. Pat. No. 3,644,564 issued on Feb. 22, 1972 and commercialized in the Shell Higher Olefins Process [SHOP].

The primary objective of the present invention is to provide a novel process for producing linear alpha-olefins using a novel catalyst system.

The process results in the production of linear alpha-olefins having 4–36 carbon atoms and particularly, is highly selective for the more useful alpha-olefins in the range of $C_4$–$C_{20}$.

Another aspect of the invention involves the high rate of conversion of ethylene to low molecular weight product olefins under controlled reaction conditions.

DISCLOSURE OF THE INVENTION

In accordance with the present invention, there is provided a process for the manufacture of linear alpha-olefins which comprises oligomerizing an unsaturated aliphatic hydrocarbon in an inert organic solvent in the presence of a catalyst mixture comprising titanium aryloxide and/or titanium alkoxide; and organoaluminum halide with or without an additive at ambient or slightly elevated temperature and at a pressure which is sufficient to maintain the solubility of the unsaturated aliphatic hydrocarbon feed and to prevent formation of branched products to produce the desired linear alpha-olefins having a narrow molecular weight distribution. It is preferred that the unsaturated aliphatic hydrocarbon is ethylene. The additive is selected from a group containing phosphorous, oxygen or sulphur compounds. If an additive is used, it can be used either singly or as a combination of two or more additives.

At least one titanium aryloxide or titanium alkoxide is used in the process of this invention. Both titanium aryloxide and titanium alkoxide can be used together. An alkyl aluminum halide may be used as the organoaluminum halide. The organoaluminum halide may be an alkylaluminum halide or alkylaluminum sesquihalide. The halide in the organoaluminum halide may be selected from chloride or bromide.

A catalyst that may be employed in the oligomerization process comprises a titanium aryl oxide and/or titanium alkoxide, organoaluminum halide and an additive such as a phosphine, phosphite, cyclic ether or a sulphur compound.

With respect to the catalyst, titanium alkoxide or titanium aryloxide may be represented as $Ti[OR]_4$ where R is defined below and all the titanium [IV] cresylates [i.e. ortho, meta or para] are preferred However, a non-limiting list of titanium aryloxides and titanium alkoxides include titanium [IV] 2,6 dimethyl phenoxide and tetra-2-ethyl hexyl titanate, triethanolamine titanate, diethanolamine titanate and the like.

The phosphorus additive in the catalyst of the present invention is preferably selected from $PPh_3$, $Ph_2PCH_2CH_2PPh_2$, $[PhO]_2P[O][OH]$ and $P[nBu]_3$.

Examples of preferred oxygenated compounds to be used in the catalyst composition are tetrahydrofuran and 1,4 dioxane.

A sulphur compound that may be employed as an additive in the tricomponent catalyst of the present invention is 2-mercaptobenzothiazole.

The titanium compound to additive molar ratio is maintained from 1:0.05 to 1:0.1. If more than one additive is used, the molar ratio of titanium compound to total additive is from 1:0.05 to 1:0.1.

It is preferred that the catalyst employed in the process of the present invention has the formula

$Ti[OR]_n[OR']_{4-n}$—$R''_xAl_2Y_{6-x}$—L wherein x=2, 3 or 4 and L is selected from the group of the additives selected from phosphorous, oxygen or sulphur compounds.

When n=4, R is

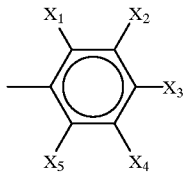

where $X_1=CH_3$; $X_2=X_3=X_4=X_5=H$,
$X_2=CH_3$; $X_1=X_3=X_4=X_5=H$,
$X_3=CH_3$; $X_1=X_2=X_4=X_5=H$, or where $X_1=CH_3$; $X_2=X_3=X_4=X_5=H$,
$X_2=CH_3$; $X_1=X_3=X_4=X_5=H$,
$X_3=CH_3$; $X_1=X_2=X_4=X_5=H$, or
$X_1=X_5=CH_3$; $X_2=X_3=X_4=H$; or R is 2-ethylhexyl or when n=2, R is triethanolamino or diethanolamino; and R' is isopropyl.

R" is ethyl or isobutyl and Y is Cl or Br.

The oligomerization reaction can be carried out at a temperature such as ambient or at slightly elevated temperatures such as 25° C.–150° C. The more preferred range being from 50° C. to 100° C. At reaction temperatures below ambient, internal, branched or polymeric products are preferably formed. Elevation in temperature enhances the formation of linear oligomeric products. However, no significant changes in alpha selectively is obtained on increase in temperature beyond the highest specified temperatures. Accordingly, temperature is one of the reaction parameters which determines the distribution and production of alpha-olefins.

During oligomerization ethylene pressures between 200 and 350 psi are preferred. Pressures between 250 and 300 psi are more preferable.

Aromatic, halogenated aromatic or aliphatic solvents can be employed as the reaction medium. Suitable solvents include n-octane, toluene, chlorobenzene, dichloromethane and the like. Toluene is especially preferred as a solvent.

Preferably during ethylene oligomerization titanium aryloxide or a titanium alkoxide and an organoaluminum halide of the catalyst are modified by phosphine, phosphite, a cyclic ether or a sulphur compound.

More preferably, the catalyst solution is prepared by reacting titanium [IV] cresylate, ethylaluminum sesquichloride and optionally P(nBu)$_3$ thereby enabling the control of ethylene oligomers to predominantly highly linear, low molecular weight products.

The linearity or the alpha-purity is the percentage weight fraction of the alpha-olefins in the total olefinic product including those cases where polymer formation was observed.

$$linearity = \frac{alpha-olefins}{alpha+internal/branched} \times 100$$

In order to obtain the desired selectivity all the reaction parameters are taken into consideration such as the composition of the catalyst, molar ratio of catalyst components, unsaturated aliphatic hydrocarbon pressure, temperature, nature of solvent and the nature of additives.

The active catalyst solution is preferably prepared in situ just prior to carrying out the oligomerization reaction. When preparing the catalyst solution the phosphorus, oxygen or sulfur compounds are added to the appropriate mixture of the titanium aryloxide and/or titanium alkoxide and organoaluminum halide. It is preferred that the titanium aryloxide and the titanium alkoxide are of the formula Ti[OR]$_4$ where R is defined above. These highly active oligomerization catalysts are transferred in the absence of oxygen and moisture to the reactor before charging the feed under pressure.

The preferred mole ratio for catalyst components titanium aryloxide and/or titanium alkoxide [e.g. Ti[OR]$_4$/Et$_3$Al$_2$Cl$_3$] to organoaluminum halide is from 1:12 to 1:18. The alpha olefin selectivity at these ratios is 93 to 99.9% in the C$_4$ to C$_{36}$ range. The titanium to aluminum mole ratio can, however, be varied from about 1:6 to 1:18.

The molar ratio of the titanium compound to the phosphorus, oxygen or sulfur compound is from 1:0.05 to 1:0.1. If more than one phosphorus, oxygen, or sulfur compound is used, the molar ratio of titanium compound to total phosphorus, oxygen and sulfur compounds is from 1:0.05 to 1:0.1.

The process of oligomerization of this invention is suitably carried out in a stainless steel autoclave having means for heating, cooling and stirring. The preferred reaction time ranges from about 10 minutes to 1 hour. The batch reactions of this process are generally quenched by injecting 3–5 ml of n-butyl alcohol. The tabulated yields of ethylene oligomers do not correspond to the actual catalyst efficiency and are based on the total weight percent of ethylene converted to products.

The process of the invention will now be described with reference to the following examples and such examples should not be construed as limiting the objectives and the scope of the invention.

EXAMPLE 1

A 300 ml stainless steel reactor [activated with high purity nitrogen for at least 2 hours at 140° C.] was charged with 0.804 grams [1.68 m mol], Ti(m-OC$_6$H$_4$CH$_3$)$_4$, 80 ml toluene and 3.84 grams [0.03 mol] EtAlCl$_2$. The vessel was pressurized with ethylene at 25° C. to 200 psi. The temperature was then increased to 50° C. and stirred (300 rpm) at this temperature for 1 hour by which time the ethylene uptake was complete indicated by a pressure drop to approximately 0 psi. A gas sample was collected and the reaction mixture containing the active catalyst was quenched with 3.0 ml n-BuOH. A liquid sample and the gas sample were analyzed by gas chromatography showing 90.2 wt % ethylene conversion and selectivity of linear olefins 1–C$_4$= 3.5, 1–C$_6$=7.8, 1–C$_8$=10.9, 1–C$_{10}$=3.7, 1–C$_{12}$=10.1, 1–C$_{14}$= 3.8, 1–C$_{16}$=3.7, 1–C$_{18}$=5.2, 1–C$_{20}$=4.9, 1–C$_{22}$=4.8, 1–C$_{24}$= 3.2, 1–C$_{26}$=2.1, 1–C$_{28}$=2.1, 1–C$_{30}$=1.4, 1–C$_{32}$=1.0, 1–C$_{34}$= 0.8; internal olefins=13 and polymer=17.4.

EXAMPLE 2

The method of example 1 was followed: The 300 ml reactor was charged with 0.71 grams, [1.5 m mol], Ti[p-

$OC_6H_4CH_3]_4$, 80 ml toluene and 6.69 grams [0.028 mol] $Et_3Al_2Cl_3$. The reaction temperature was maintained at 100° C. and the ethylene charged to have a pressure of 200 psi in the vessel. The weight of alpha olefins was 10.9 grams after 1 hour at 99.4 wt % conversion and linear olefin selectivity $1-C_4=13.9$, $1-C_6=15.9$, $1-C_8=17.4$, $1-C_{10}=7.2$, $1-C_{12}=6.5$, $1-C_{14}=5.5$, $1-C_{16}=5.5$, $1-C_{18}=5.0$, $1-C_{20}=4.2$, $1-C_{22}=3.6$, $1-C_{24}=2.9$, $1-C_{26}=2.5$, $1-C_{28}=2.2$, $1-C_{30}=3.3$, $1-C_{32}=1.8$, $1-C_{34}=1.6$.

EXAMPLE 3

The procedure of example 1 was followed: In a 300 ml stainless steel reactor there was placed 0.74 grams, [1.40 m mol], $Ti[p-OC_6H_3-2,6-Me_2]_4$, 80 ml toluene and 6.2 grams [0.025 moll $Et_3Al_2Cl_3$. Ethylene was charged into the vessel to 200 psi pressure at a reaction temperature of 150° C. The reaction was terminated after 15 minutes and the products analyzed as in example 1. The yield of pure alpha olefins was 8.5 grams at 99.2 wt % conversion and an alpha olefin distribution showing $1-C_4=4.7$, $1-C_6=19.1$, $1-C_8=16.5$, $1-C_{10}=11.3$, $1-C_{12}=10.9$, $1-C_{14}=18.8$, $1-C_{16}=7.4$, $1-C_{18}=5.3$, $1-C_{20}=4.3$, $1-C_{22}+=1.14$.

EXAMPLE 4

The procedure of example 1 was followed: In a 300 ml stainless steel reactor there were added a catalyst solution containing 0.685 grams, [1.44 m mol], $Ti[p-OC_6H_4CH_3]_4$, 80 ml toluene, 0.26 mol $Et_3Al_2Cl_3$ and 0.14 mol tetrahydrofuran (THF). Ethylene was pressurized to 350 psi. After 1 hour reaction at 150° C. the total yield of linear alpha olefins was 13.9 grams at 99.4 wt % ethylene conversion. The analysis showed the following alpha olefin selectivity $1-C_4=5.5$, $1-C_6=8.5$, $1-C_8=17.6$, $1-C_{10}=11.6$, $1-C_{12}=11.4$, $1-C_{14}=9.6$, $1-C_{16}=7.7$, $1-C_{18}=6.0$, $1-C_{20}=4.3$, $1-C_{22}+=12.9$ and polymer=4.7.

EXAMPLE 5

For the purpose of comparison, example 1 was followed. Chlorobenzene was employed as the solvent for preparing the catalyst consisting of 0.78 grams, [1.64 m mol], $Ti[p-OC6H_4CH_3]_4$ and 7.3 grams [0.029 mol] $Et_3Al_2Cl_3$. Ethylene was then charged to the reactor maintained at 50° C. to a pressure of 200 psi. After 1 hour the wt % ethylene conversion was 97.5% and the alpha olefin yield 7.8 grams with the following selectivity $1-C_4=18.8$, $1-C_6=19.0$, $1-C_8=24.4$, $1-C_{10}=10.5$, $1-C_{12}=8.1$, $1-C_{14}=5.1$, $1-C_{16}=3.7$, $1-C_{18}=2.5$, $1-C_{20}=2.0$, $1-C_{22}+=5.5$.

The catalyst system employed in the process of the present invention and illustrated in examples 1 to 5 is influenced by the nature of R in $Ti[OR]_4$, the reaction temperature, cocatalyst/catalyst ratio and the nature of the additive. Tables I–III summarize and compare the results of ethylene oligomerization under different conditions.

TABLE 1

Ethylene oligomerization with titanium [IV] cresylates

| Run No. | Catalyst | Conv. % | ∝-olefin % $C_4$–$C_{36}$ | Polymer % |
|---|---|---|---|---|
| 1. | $Ti(\underline{o}-OC_6H_4CH_3)_4$ | 97.8 | 99.8 | 0.01 |
| 2. | $Ti(\underline{m}-OC_6H_4CH_3)_4$ | 98.9 | 98.0 | 2.0 |
| 3. | $Ti(p-OC_6H_4CH_3)_4$ | 98.2 | 99.4 | 0.6 |
| $^PC_2H_4$ | 200 psi | | | |

TABLE 1-continued

Ethylene oligomerization with titanium [IV] cresylates

| Run No. | Catalyst | Conv. % | ∝-olefin % $C_4$–$C_{36}$ | Polymer % |
|---|---|---|---|---|
| TEMPERATURE | 100° C. | | | |
| COCATALYST | $Et_3Al_2Cl_3$ | | | |
| SOLVENT | Toluene | | | |

Cocatalyst/Catalyst molar ratio 18; Reaction time 60 minutes

TABLE II

Oligomerization of ethylene with titanium [IV] aryl oxides or titanium alkoxides

| Run No. | Catalyst | Temp. ° C. | Conv. % | ∝-olefin % $C_4$–$C_{36}$ | Polymer % |
|---|---|---|---|---|---|
| 1. | $Ti(m-OC_6H_4CH_3)_4$ | 50 | 98.1 | 98.4 | 1.6 |
| 2. | $Ti(OCH_2CH(Et)(CH_2)_3Me)_4$ | 50 | 92.4 | 97.7 | 2.3 |
| 3. | Triethanolamine titanate | 50 | 98.7 | 99.1 | 0.9 |
| 4. | Diethanolamine titanate | 50 | 97.5 | 64.1 | 35.9 |
| 5. | $Ti(OC_6H_3-2,6-Me_2)_4$ | 50 | 98.9 | 92.7 | 7.5 |
| $^PC_2H_4$ | 200 psi | | | | |
| COCATALYST | $Et_3Al_2Cl_3$ | | | | |
| SOLVENT | Toluene | | | | |

Cocatalyst/Catalyst molar ratio 18; Reaction time 60 minutes

TABLE III

Influence of additives on ethylene oligomerization

| Run No. | Additive | Conv. % | ∝-olefin % | Polymer % |
|---|---|---|---|---|
| 1. | $P(n-Bu)_3$ | 99.6 | 99.9 | Nil |
| 2. | $PPh_3$ | 93.3 | 97.9 | Nil |
| 3. | THF | 99.3 | 95.3 | 4.6 |
| 4. | 1,4 dioxane | 99.9 | 65.3 | 34.7 |
| 5. | 2-mercaptobenzothiazole | 93.1 | 79.9 | 20.1 |
| $^PC_2H_4$ | 350 psi | | | |
| TEMPERATURE | 150° C. | | | |
| CATALYST | $Ti(\underline{p}-OC_6H_4Me)_4$—$Et_3Al_2Cl_3$; | | | |
| SOLVENT | Toluene | | | |

Cocatalyst/Catalyst molar ratio 18; Reaction time 60 minutes; Additive/Titanium 0.1 (molar ratio)

EXAMPLE 6

The method of Example 1 was followed. The reactor was charged with $Ti(m-OC_6H_4CH_3)_4$ and $Et_2AlCl$ in such a proportion that Al/Ti=18. The ethylene conversion after 1h was 96.5% (wt) and selectively to linear alpha olefins are $1-C_4=11.8$, $1-C_6=4.6$, $1-C_8=2.4$, $1-C_{10}=4.1$, $1-C_{12}=5.7$, $1-C_{14}=6.7$, $1-C_{16}=6.4$, $1-C_{18}=6.3$, $1-C_{20}=5.7$, $1-C_{22}=5.2$, $1-C_{24}=4.4$, $1-C_{26}=4.1$, $1-C_{28}=3.8$, $1-C_{30}=3.5$, $1-C_{32}=3.1$, $1-C_{34}=2.8$ and polymer=19.4.

EXAMPLE 7

The method of example 1 was followed: The 300 ml reactor was charged with 0.8g [1.68 mmole] $Ti[OC_6H_4CH_3]_4$, 80 ml toluene and 5.38g [0.03 mole] I-$Bu_2AlCl$. The vessel was pressurized with ethylene at 25° C. to 200 psi. The reaction temperature increased to 50° C. and stirred at this temperature for 1h. The ethylene was fully converted into the oligomers. Selectivity to alpha olefins are $1-C_4=$ 24.1, 1-$C_6$=6.4, 1-$C_{10}$=4.8, 1-$C_{12}$=6.8, 1-$C_{14}$=7.7, 1-$C_{16}$=7, 1-$C_{18}$=6.3, 1-$C_{20}$=5.3, 1-$C_{22}$=4.2, 1-$C_{24}$=3.5, 1-$C_{26}$=2.8, 1-$C_{28}$=2.4, 1-$C_{30}$=2.1, 1-$C_{32}$=1.7, 1-$C_{34}$=1.1, internal olefins=3.7 and polymer=9.8.

EXAMPLE 8

The method of example 1 was followed. In a 300 ml stainless steel reactor there were added 0.8 g [1.68 mmole], Ti(OC$_6$H$_4$CH$_3$)$_4$, 80 ml toluene, 7.69 g [0.03 mole] I-Bu$_2$AlBr. Ethylene was pressurized to 200 psi. After 1 h reaction at 50° C. the ethylene was fully converted into oligomers. Selectivity to alpha olefins are 1-$C_4$=27, 1-$C_6$=6.1, 1-$C_8$=7.5, 1-$C_{10}$=4.9, 1-$C_{12}$=5.7, 1-$C_{14}$=5.7, 1-$C_{16}$=4.9, 1-$C_{18}$=4.3, 1-$C_{20}$=3.3, 1-$C_{22}$=2.4, 1-$C_{24}$=1.8, 1-$C_{26}$=1.3, 1-$C_{28}$=1.2, 1-$C_{30}$=0.8, 1-$C_{32}$=0.5, internal olefins—3.4 and polymer 18.9.

Examples 1, 5 and 6 refer to different ethylaluminum chlorides (EtAlCl$_2$, Et$_3$Al$_2$Cl$_3$ and Et$_2$AlCl]) that can be used in the reaction. Examples 6 and 7 refer to different alkylaluminum aluminum chlorides (Et$_2$AlCl and I-Bu$_2$AlCl) that can be employed in the reaction. Finally, examples 7 and 8 cover iso-butyl aluminum halides (I-Bu$_2$AlCl & I-Bu$_2$AlBr) that can be used in the oligomerization of ethylene.

The foregoing description and the examples are provided for the purpose of guiding persons skilled in the art and it must be appreciated that the invention is not restricted thereto. Other modifications in the embodiments of the invention are clearly possible within the scope of what has been discussed herein.

We claim:

1. A process for the manufacture of linear alpha-olefins which comprises oligomerizing unsaturated aliphatic hydrocarbons in an inert organic solvent in the presence of a catalyst consisting essentially of a titanium component and an organoaluminum halide component said titanium component selected from the group consisting of titanium aryloxide and titanium alkoxide at ambient or slightly elevated temperature in the range of 25° C. to 150° C. and at a pressure to maintain the solubility of the unsaturated aliphatic hydrocarbon and to prevent formation of branched products to produce linear alpha-olefins having a narrow molecular weight distribution.

2. The process as claimed in claim 1 wherein the unsaturated aliphatic hydrocarbon is ethylene.

3. The process according to claim 1 wherein the ratio of titanium aryloxide and/or titanium alkoxide to organoaluminum halide is from 1:6 to 1:18.

4. The process according to claim 1 wherein the ratio of titanium aryloxide and/or titanium alkoxide to the additives is 1:0.05 to 1:0.1.

5. The process as claimed in claim 1 wherein the oligomerization temperature is from 25° C.–150° C.

6. The process as claimed in claim 1 wherein the pressure is from 200 psi to 350 psi.

7. The process as claimed in claim 1 wherein the organic solvent is an aromatic, halogenated aromatic or a halogenated aliphatic hydrocarbon solvent.

8. The process as claimed in claim 1 wherein the organoaluminum halide is selected from alkylaluminum halide or alkylaluminum sesquihalide.

9. The process as claimed in claim 8 wherein the halide function in said organo aluminum halide is chloride or bromide.

10. The process according to claim 1 wherein the linear alpha-olefins are $C_4$–$C_{38}$ alpha-olefins.

11. A process for the manufacture of linear alpha-olefins which comprises oligomerizing an unsaturated aliphatic hydrocarbon in an inert organic solvent in the presence of a catalyst of the formula

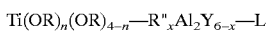

wherein x=2, 3 or 4 and L is selected from the group consisting of phosphorus, oxygen and sulfur compounds and when n is 4, R is

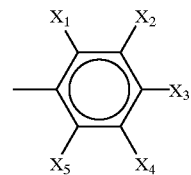

where
$X_1$=CH$_3$; $X_2$=$X_3$=$X_4$=$X_5$=H,
$X_2$=CH$_3$; $X_1$=$X_3$=$X_4$=$X_5$=H,
$X_3$=CH$_3$; $X_1$=$X_2$=$X_4$=$_5$H, or
$X_1$=$X_5$=CH$_3$; $X_2$=$X_3$=$X_4$=H or R is 2-ethylhexyl or when n=2, R is triethanolamino or diethanolamino; and R' is isopropyl, and R" is ethyl or isobutyl and Y=Cl or Br at ambient or slightly elevated temperature in the range of 25° C. to 150° C. and at a pressure in the range of 200 psi to 350 psi which is sufficient to maintain the solubility of the unsaturated aliphatic hydrocarbon to prevent formation of branched products to produce linear alpha-olefins having a narrow molecular weight distribution.

12. The process as claimed in claim 11 wherein the organic solvent is an aromatic, halogenated aromatic or a halogenated aliphatic hydrocarbon solvent.

13. A process as claimed in claim 11 wherein the organo aluminum halide is selected from alkylaluminum halide or alkylaluminum sesquihalide.

14. A process as claimed in claim 13 wherein the halide function in said organo aluminum halide is chloride or bromide.

15. A process as claimed in claim 11 wherein the phosphorous compound is selected from the group consisting of P[nBu]$_3$, PPh$_3$, Ph$_2$PCH$_2$CH$_2$ PPH$_2$ and (PhO)$_2$P(O)(OH).

16. The process as claimed in claim 11 wherein the oxygen compound is selected from tetrahydrofuran, 1,4 dioxane or a cyclic ether.

17. The process as claimed in claim 11 wherein the sulphur compound is 2-mercaptobenzothiazole.

18. The process as claimed in claim 11 wherein the unsaturated aliphatic hydrocarbon is ethylene.

19. A process for the manufacture of linear alpha-olefins which comprises oligomerizing unsaturated aliphatic hydrocarbons in an inert organic solvent in the presences of a catalyst consisting essentially of a titanium component, an organoaluminum component and an additive, said titanium component selected from the group consisting of titanium aryloxide and titanium alkoxide, and said additive selected from the group consisting of phosphorous, oxygen and sulfur compounds, at ambient or slightly elevated temperature in the range of 25° C. tp 150° C. and at a pressure to maintain the solubility of the unsaturated aliphatic hydrocarbon and to prevent formation of branched products to produce linear alpha-olefins having a narrow molecular weight distribution.

20. The process as claimed in claim 19 wherein the unsaturated aliphatic hydrocarbon is ethylene.

21. The process as claimed in claim 19 wherein said catalyst has the formula $$Ti(OR)_n(OR')_{4-n}\text{---}R''_xAl_2Y_{6-x}\text{---}L$$

wherein x=2, 3 or 4 and L is the additive; and when n is 4, R is

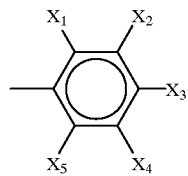

where
- $X_1=CH_3$; $X_2=X_3=X_4=X_5=H$,
- $X_2=CH_3$; $X_1=X_3=X_4=X_5=H$,
- $X_3=CH_3$; $X_1=X_2=X_4=X_5=H$, or
- $X_1=X_5=CH_3$; $X_2=X_3=X_4=H$; or R is 2-ethylhexyl or when n=2, R is triethanolamino or diethanolamino; and R' is isopropyl and R" is ethyl or isobutyl and Y=Cl or Br.

22. The process as claimed in claim 19 wherein the phosphorous compound is selected from the group consisting of $P(nBu)_3$, $PPh_3$, $Ph_2 PCH_2CH_2PPH_2$ and $(PhO)_2P(O)(OH)$.

23. The process as claimed in claim 19 wherein the oxygen compound is tetrahydrofuran, 1,4 dioxane or any cyclic ether.

24. The process as claimed in claim 19 wherein the sulphur compound is 2-mercaptobenzothiazole.

* * * * *